(12) United States Patent
Song (10) Patent No.: US 6,607,493 B2
(45) Date of Patent: Aug. 19, 2003

(54) HEART BEAT ANALYSIS DEVICE AND METHOD

(75) Inventor: O. Shik Song, Taegu (KR)

(73) Assignee: Hyunwon Inc. (KR)

( * ) Notice: Subject to any disclaimer, the term of this patent is extended or adjusted under 35 U.S.C. 154(b) by 0 days.

(21) Appl. No.: 09/880,595

(22) Filed: Jun. 13, 2001

(65) Prior Publication Data

US 2002/0115937 A1 Aug. 22, 2002

(30) Foreign Application Priority Data

Feb. 16, 2001 (KR) .......................................... 2001-7787

(51) Int. Cl.⁷ .................................................. A61B 5/02
(52) U.S. Cl. ...................... 600/502; 600/300; 600/481; 600/500; 600/508; 482/8; 482/9; 482/148; 482/910
(58) Field of Search ................................. 600/300–301, 600/481, 500–504, 508, 509; 482/8–9, 901–902, 909–910, 148

(56) References Cited

U.S. PATENT DOCUMENTS

| | | | | |
|---|---|---|---|---|
| 4,301,808 A | * | 11/1981 | Taus | 600/500 |
| 4,406,290 A | * | 9/1983 | Walbeoffe-Wilson et al. | 600/502 |
| 4,436,097 A | * | 3/1984 | Cunningham | 482/8 |
| 4,776,323 A | * | 10/1988 | Spector | 600/502 |
| 4,828,257 A | * | 5/1989 | Dyer et al. | 482/5 |
| 5,314,389 A | * | 5/1994 | Dotan | 482/3 |
| 5,387,164 A | * | 2/1995 | Brown, Jr. | 482/9 |
| 5,410,472 A | * | 4/1995 | Anderson | 482/9 |
| 5,474,077 A | * | 12/1995 | Suga | 600/500 |
| 5,527,239 A | * | 6/1996 | Abbondanza | 482/9 |
| 5,706,822 A | * | 1/1998 | Khavari | 600/483 |
| 5,738,104 A | * | 4/1998 | Lo | 600/521 |
| 5,807,267 A | * | 9/1998 | Bryars et al. | 600/519 |
| 6,013,009 A | * | 1/2000 | Karkanen | 600/500 |
| 6,132,337 A | * | 10/2000 | Krupka et al. | 600/520 |
| 6,230,047 B1 | * | 5/2001 | McHugh | 600/500 |

\* cited by examiner

*Primary Examiner*—Robert L. Nasser
*Assistant Examiner*—Patricia C. Mallari
(74) *Attorney, Agent, or Firm*—Harness, Dickey & Pierce, P.L.C.

(57) ABSTRACT

The present invention disclosed relates to heart beat analysis device and method capable of measuring the heart beats of an individual in physical exercise, notifying the individual of a suitable exercise amount with messages or warning sounds, and allowing the individual to listen to the radio or music.

10 Claims, 5 Drawing Sheets

HEART BEAT ANALYSIS DEVICE AND METHOD

Reference to Related Patents Applications

U.S. Pat. No. 6,036,653 Pulsimeter
U.S. Pat. No. 5,650,982 Pulsimeter provided with or without a pedometer
U.S. Pat. No. 5,640,965 Pulsimeter capable of properly evaluating amount of exercise at arbitrary time
U.S. Pat. No. 5,539,706 Pulsimeter provided with or without a pedometer
U.S. Pat. No. 5,509,422 Clinical thermometer with pulsimeter
U.S. Pat. No. 5,190,047 Photoelectric pulsation type pulsimeter
U.S. Pat. No. 4,929,825 Means for detecting damage to the card connecting the photosensor and main body pulsimeter
U.S. Pat. No. 4,715,384 Pulsimeter
U.S. Pat. No. 4,572,207 Pulsimeter for vehicles
U.S. Pat. No. 4,120,296 Pulsimeter

BACKGROUND OF THE INVENTION

1. Field of the Invention

The present invention relates to heart beat analysis device and method, and more particularly to heart beat analysis device and method capable of measuring the heart beats of an individual in physical exercise, notifying the individual of a suitable exercise amount with messages or warning sounds, and allowing the individual to listen to the radio or music.

2. Description of Related Art

Various physical exercises and, in particular, jogging being done by individuals with different ages and health factors become effective only in a range of heart beat rates required for the individuals.

That is, in case that individual heart beat rates do not drop to a specific low level, physical exercises can have a slight influence on them, whereas, in case that the individual heart beat rates go beyond a upper limit level, the exercises can have a harmful influence on them definitely. Accordingly, people who start physical exercise perform exercise amounts suitable for them according to their physical status and their usual exercise amounts. The most basic of the exercise amount measurements measure the number of heart beats of an individual in exercise, and compare the measured number with a standard table, so that he measures his physical exercise as weak, medium, or strong for himself.

A conventional heart beat analysis device requires its user himself to measure his heart beats based on existing data and to adjust the exercise strength accordingly.

Further, it has a problem in that he can not analyze what exercise is suitable for himself unless he records the heart beat measurement data by himself.

Furthermore, it has another problem in that individuals in physical exercise get easily bored during the exercise due to its simplicity.

SUMMARY OF THE INVENTION

In order to solve the above problems, it is an object of the present invention to provide heart beat analysis device and method which prevent individuals from excessive exercises by sending warning signals to the individuals in case of exceeding predetermined exercise amounts through individuals' heart beat measurements.

Further, it is another object of the present invention to provide heart beat analysis device and method which allow individuals in physical exercise to listen to the radio or music in order to prevent them from easily getting dull.

Furthermore, it is a further object of the present invention to provide heart beat analysis device and method which can store the heart beat changes of individuals in physical exercise, analyze heart beat changes according to individuals' exercise states by transferring the changes to personal computers (PCs) later, and simultaneously measure exercise effects.

In order to achieve the above objects, the present invention comprises a unit for measuring heart beats of a user in physical exercise; and a unit having a heart beat signal processing unit, and for analyzing heart beat signals measured from the heart beat measurement unit, comparing the analyzed heart beat signals with reference values, outputting warning messages when in excessive exercise, and outputting guidance messages when in insufficient exercise.

Further, the present invention comprises steps of (1) inputting and storing reference values as to the number of heart beats; (2) measuring heart beats of a user in physical exercise; and (3) comparing the heart beat measurement value measured in step (2) with the reference values as to the number of heart beats, and outputting a warning signal in case that the heart beat measurement value is below a lower limit value or above an upper limit value of the reference values.

Digital music files to be retrieved in the above are files having extensions of mp3, ra, mid, rmi, asf, wav, and so on.

BRIEF DESCRIPTION OF THE DRAWINGS

The above objects and other advantages of the present invention will become more apparent by describing in detail a preferred embodiment thereof with reference to the attached drawings, in which.

DETAILED DESCRIPTION OF THE PREFERRED EMBODIMENT

Hereinafter, the present invention will be described in more detail with reference to the accompanying drawings showing a preferable embodiment of the present invention.

Figure 1:
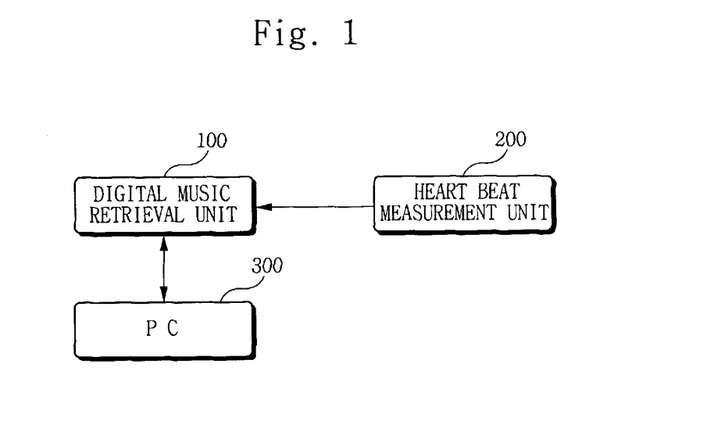
FIG. 1 is a view for showing a structure of a heart beat analysis device according to an embodiment of the present invention.

FIG. 1 is a block diagram for schematically showing a structure of a heart beat analysis device according to an embodiment of the present invention.

As shown in FIG. 1, the present invention includes a digital music retrieval unit 100 and a heart beat measurement unit 200. Further, a personal computer(PC) 300 shown in FIG. 1 is provided to receive and analyze heart beat information of a user in physical exercise.

The digital music retrieval unit 100 stores and outputs digital music as well as receives and outputs radio broadcasts.

Further, the digital music retrieval unit 100 performs the functions of receiving and storing heart beat information of a user in physical exercise and outputting warning messages as to whether the exercise is insufficient or excessive. Each component of the digital music retrieval unit 100 of performing such functions will be described in more detail in FIG. 2.

The digital music retrieval unit 100 may be manufactured to be hung around the neck of a user by a string like a stop watch. Further, it may be manufactured to be attached on the front of the user's sporting coat. Furthermore, it may be manufactured to be worn on the wrist like a wrist watch in one body with the heart beat measurement unit 200.

In the meantime, the digital music retrieval unit 100 may be realized to have only a digital music retrieval function, to have only a function of receiving radio broadcasts, or to have only a function of outputting warnings or messages as to excessive or insufficient exercises to a user by receiving, storing, and analyzing heart beat information measured from the heart beat measurement unit 200.

Next, the heart beat measurement unit 200 is connected to the digital music retrieval unit 100 in a wire or wireless way, and performs a function of measuring heart beats of a user in physical exercise and transferring the measured heart beats to the digital music retrieval unit 100. The internal structural components of the heart beat measurement unit 200 will be described in more detail below with reference to FIG. 3. Such heart beat measurement unit 200 may be structured to be carried on a wrist like a wrist watch.

The personal computer 300 is connected to the digital music retrieval unit 100 by an interface as a communication unit for exchanging data, and performs functions of transferring digitalized music files to the digital music retrieval unit 100, measuring user's exercise effects by receiving and analyzing heart beat information of a user in physical exercise which is stored in the digital music retrieval unit 100, and preparing an exercise schedule for improving the exercise effects. A data analysis is performed for a change rate of the number of heart beats by time (second/minute/hour), a change rate of the number of heart beats by unit time (day/month/year), a suitable exercise direction proposal based on a change of the number of heart beats, a proposal of the objective heart beats (a proper exercise amount) based on ages, sex, heights, and weights, an indication of an exercise improvement degree based on the change of the number of heart beats, a total amount of calories consumed during exercise, what percent of the total consumed calories amount comes from the body fat, and so on.

The personal computer 30 for carrying out such functions is a general personal computer which carries out heart beat measurement data analysis by using a certain program realized to analyze heart beats.

Next, a description will be made on each component of the digital music retrieval unit and operations of each component thereof with reference to FIG. 2.

Figure 2:
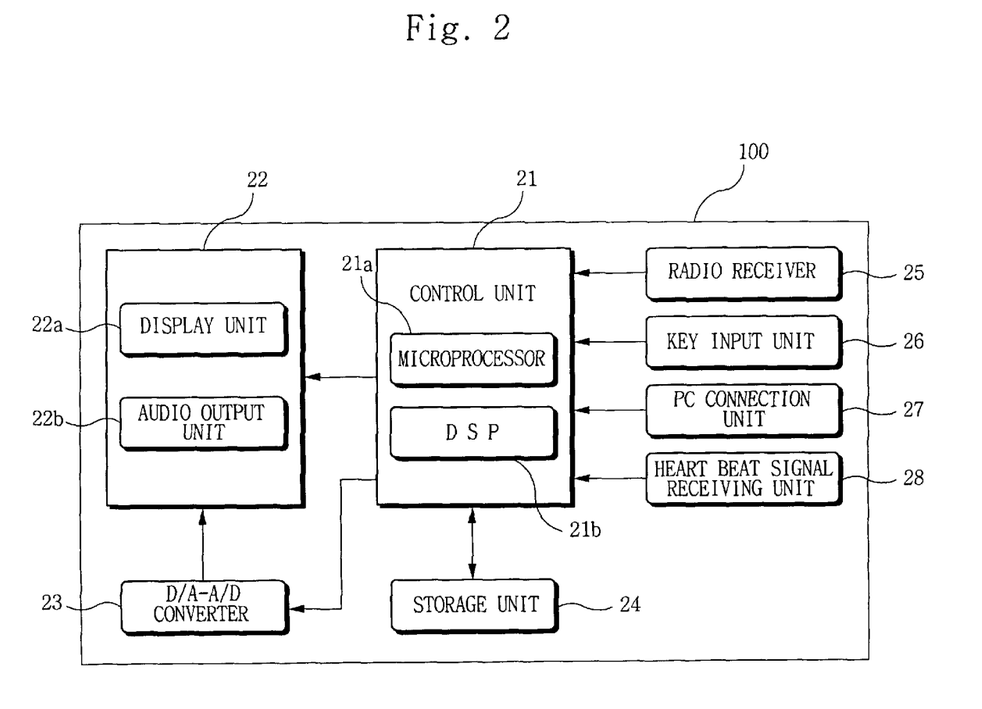
FIG. 2 is a block diagram for showing an internal structure of a digital music retrieval unit of FIG. 1.

FIG. 2 is a block diagram for showing the structural component of the digital music retrieval unit 100 out of the entire structural components of FIG. 1 according to an embodiment of the present invention.

As shown in FIG. 2, the digital music retrieval unit according to the present invention has a control unit 21, an output unit 22, a digital-analog/analog-digital (D/A–A/D) converter 23, a storage unit 24, a radio receiver 25, a key input unit 26, a PC connection unit 27, and a heart beat signal receiving unit 28. The control unit 21 includes a microcomputer 21a and a digital signal processor (DSP) 21b. The output unit 22 has an indication unit 22a and an audio output unit 22b.

Hereinafter, operations of the digital music retrieval unit will be described in detail.

The heart beat signal receiving unit 28 receives heart beat information measured from the heart beat measurement unit and transfers it to the control unit 21.

At this time, the control unit 21 stores the number of heart beats received into a storage unit 24, analyzes the number of heart beats received, compares it with a predetermined comparison value, and outputs warning messages by using characters or voices to a user. At this time, the warning messages may be outputted in characters through the indication unit 22a of the output unit 22 or in voices through the audio output unit 22b.

For an instance, the maximum number of heart beats is calculated based on a user's age. At this time, an arithmetic formula used is "the maximum number of heart beats=220–age".

Next, the objective number of heart beats is calculated. The objective number of heart beats means a reference value range which can evaluate what extent of heart beats corresponds to a high-strength exercise, a medium-strength exercise, or a low-strength exercise.

An arithmetic formula used at this time is "the objective number of heart beats=the maximum number of heart beats*% exercise strength".

In the exercise strengths, the reference values can be established by:

High-strength: 85%~100%
Medium-strength: 70%~85%
Low-strength: 50%~70%.

Accordingly, the control unit 21 inputs the number of heart beats of a user(an individual in physical exercise) from the heart beat measurement unit 200, compares the inputted number of heart beats with the calculated objective number of heart beat, and judges that the exercise corresponds to the low-strength, medium-strength, or high-strength.

Further, in general, physical exercise begins with the low-strength for an initial exercise start(a timer can be used to judge if the physical exercise is in an initial state), moves to the medium-strength for main exercise, and back to the low-strength for final exercise. Accordingly, the control unit 21 outputs a warning sound if a physical exercise strength abruptly increases to the medium-strength or to the high strength in the beginning of exercise. The control unit 21 judges if the main exercise is being carried out with the medium strength. The control unit 21 outputs a warning signal to ask for speeding up more if judged as the low strength, and for adjusting exercise pace if judged as the high strength. Further, the control unit 21 judges if the final exercise is being carries out with the low strength, and asks for speeding down more if judged as the medium strength.

At this time, such exercise patterns can be selected by a user, or provided as one instance, and, in case of a user's option, the heart beat analysis unit shows various options to the user to select one.

The control unit 21 may indicate on the indication unit 22a or output in voices by using the audio output unit 22b whether a present exercise state is the initial exercise state, main exercise state, or final exercise state, as well as whether the exercise is being carried out with the low, medium, or high strength.

Further, the control unit 21 may display the number of heart beats received on the indication unit 22a or output it in voice. The control unit 21 may display present time on the indication unit 22a by receiving the present time from a timer, and display exercise period of time on the unit 22a.

The control unit 21 digital-signal-processes and retrieves digital music if a digital music retrieval mode is selected through the key input unit 26, so that a user in physical exercise can listen to the music he wants.

The control unit 21, if a radio reception mode is selected through the key input unit 26, signal-processes and outputs radio signals received from the radio receiver 25.

In the meantime, the PC connection unit 27 is connected to an external personal computer, enabling data communications.

The control unit 21 out of the above components includes the microcomputer 21a and the digital signal processor (DSP) 21b.

The microcomputer 21a, if a user selects the radio reception mode or digital music retrieval mode by using the key input unit 26, changes the modes of the digital music retrieval unit 100 based on a selected signal. If a user inputs a set value, for example, an age, for his physical exercise through the key input unit 26, the microcomputer 21a calculates the maximum number of heart beats and stores the set value and the maximum number of heart beats calculated in the storage unit 24, accordingly.

Further, the microcomputer 21a uses the preset maximum number of heart beats of a user which is stored in the storage unit 24, calculates the objective number of heart beats, compares the objective number of heart beats with a heart beat measurement signal inputted from the external heart beat measurement unit 200, outputs warning messages based on a user's exercise amount or messages as to an insufficient exercise amount and the like, and stores in the storage unit heart beat measurement data received from the heart beat signal receiving unit 28.

The DSP 21b performs a digital signal process and retrieves digital music files. If a user selects the digital music retrieval mode through the key input unit 26, the control unit 26 reads out digital music files stored in the storage unit 24 and transfers them to the DSP 21b constructed in the control unit 21. The digital music files are digital-signal-processed by the DSP 21b, converted into analog signals by the D/A–A/D converter 23, and outputted to the audio output unit 22b. At this time, the digital music files may be realized for a user to select for a retrieval, or realized to be retrieved based on an exercise state. That is, it may be realized to provide a slight slow temp music for a low-strength exercise, a fast temp music for a medium- and high-strength exercise, and music for relaxing soul and body for a final exercise.

The output unit 22 includes the indication unit 22a for a visual interface with a user and an audio output unit 22b for an auditory interface. An LCD display device may be employed as the indication unit 22a.

The key input unit 26 has keys for retrieval, volume control, fast forward (FF), rewind (REW), mode setting (MODE), hold (HOLD), and plural characters and numbers. Here, the mode setting key allows a user to select and adjust a digital music retrieval mode, radio broadcast reception mode, heart beat measurement reference setting mode, and PC data communication mode.

If the digital music retrieval mode is selected by the mode setting key, the digital music retrieval unit is converted into the digital music retrieval mode, if the radio broadcast reception mode is selected, the digital music retrieval unit is converted to output radio broadcasts received through the radio receiver 25, if the heart beat measurement reference setting mode is selected, the digital music retrieval unit is converted into a mode for setting reference conditions for measuring heart beats by a user, and, if the PC data communication mode is set, a conversion is made to enable data exchanges to be controlled between the digital music retrieval unit and a PC. Such mode changes can be outputted to the indication unit 22a constructed in the output unit 22 to be selected, and a mode can be directly selected by the mode setting key to carry out a corresponding function.

In the heart beat measurement reference setting mode as stated above, upper and lower limit values of heart beats to be measured in physical exercise are set in order that the values can be used as references for outputting warnings or messages, and a selection is made on whether a heart beat measurement value is stored or not, which is a condition for storing a heart beat measurement value in a memory. Further, the objective number of heart beats can be automatically set by enabling an age, sex, height, and weight of a user, that is, an individual in physical exercise to be inputted, and, if physical exercise is not carried out within a set period of time, messages are produced. Furthermore, setting is made to measure a total amount of calories consumed in physical exercise and what percent of the total calories consumed comes from the body fat.

In the PC data communication mode as stated above, a menu is selected which can download digital music files to the radio receiver and digital music retrieval unit from the personal computer 300, and a menu is selected which can upload to the personal computer 300 the heart beat data stored in the digital music retrieval unit 100. A user can transfer necessary digital music files to the radio receiver and digital music retrieval unit 100 from the personal computer, as well as transfer the heart beat measurement data during physical exercise from the storage unit 24 of the digital music retrieval unit 100 to the personal computer 300 in order to analyze an effect of the physical exercise in more detail.

Communication interfaces such as RS-232C, RJ-11, RJ-45, or the like can be used as the communication interfaces built in the PC connection unit 27 to communicate data with the personal computer 300, and communications based on infrared LAN cards or infrared communication ports are available as well.

The heart beat signal receiving unit 28 receives heart beat measurement data from the heart beat measurement unit 200 in a wire or wireless way. In case of wire, data is received through a certain cable, and, in case of wireless, receptions are carried out by using a wireless signal such as an RF signal and the like.

Figure 3:
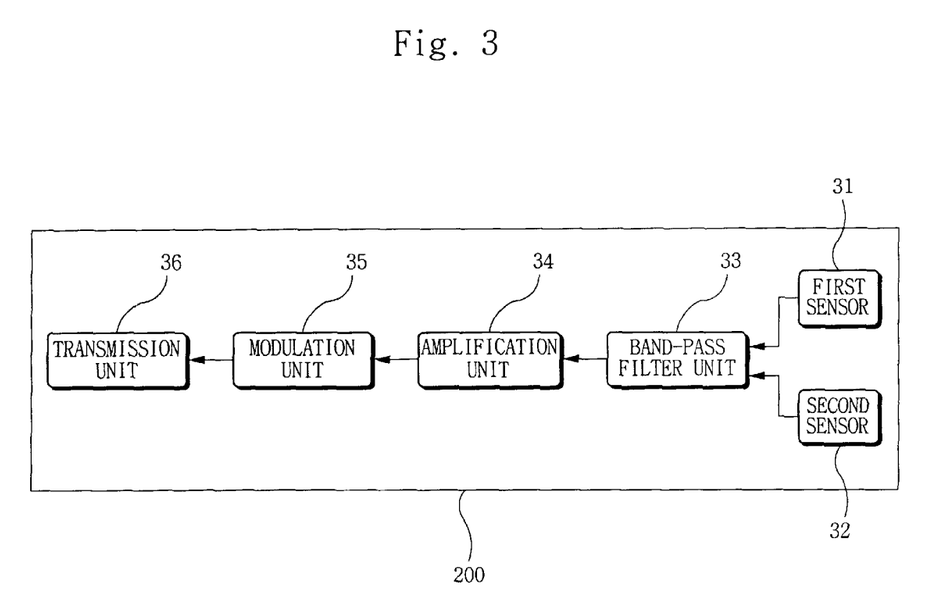
FIG. 3 is a view for showing an internal structure of the heart beat analysis device of FIG. 1.

FIG. 3 is a block diagram for showing an internal structure of the heart beat measurement unit 200 of FIG. 1.

As shown in FIG. 1, the heart beat measurement unit 200 according to the present invention includes first and second sensors 31 and 32 for measuring minute current flowing in a user (an individual in physical exercise) or heart beats and converting the measurement into an electric signal, a band-pass filter unit 33 for extracting necessary signals from signals measured from the first and second sensors 31 and 32, an amplification unit 34 for amplifying the signals filtered in the band-pass filter unit 33, a modulation unit 35 for modulating the amplified signals into a signal necessary for transmission, and a transmission unit 36 for transmitting the modulated signal to the digital music retrieval unit 100.

Conventional sensors such as pressure sensors like strain gauges, minute current measurement sensors having positive and negative values, or photo sensors may be used as the first and second sensors 31 and 32.

The heart beat measurement unit 200 extracts effective signals through the band-pass filter unit 33 from signals detected by the first and second sensors 31 and 32, and amplifies the extracted signal to a certain level through the amplification unit 34. In case that the amplified signal is transferred in a wireless way, the heart beat measurement unit 200 converts the amplified signal into an RF signal through a modulation process for transmission, and, in case of the amplified signal is transferred in a wire way, the heart beat measurement unit 200 transfers the amplified signal to the radio receiver and digital music retrieval unit 100 through a wire.

Figure 4:
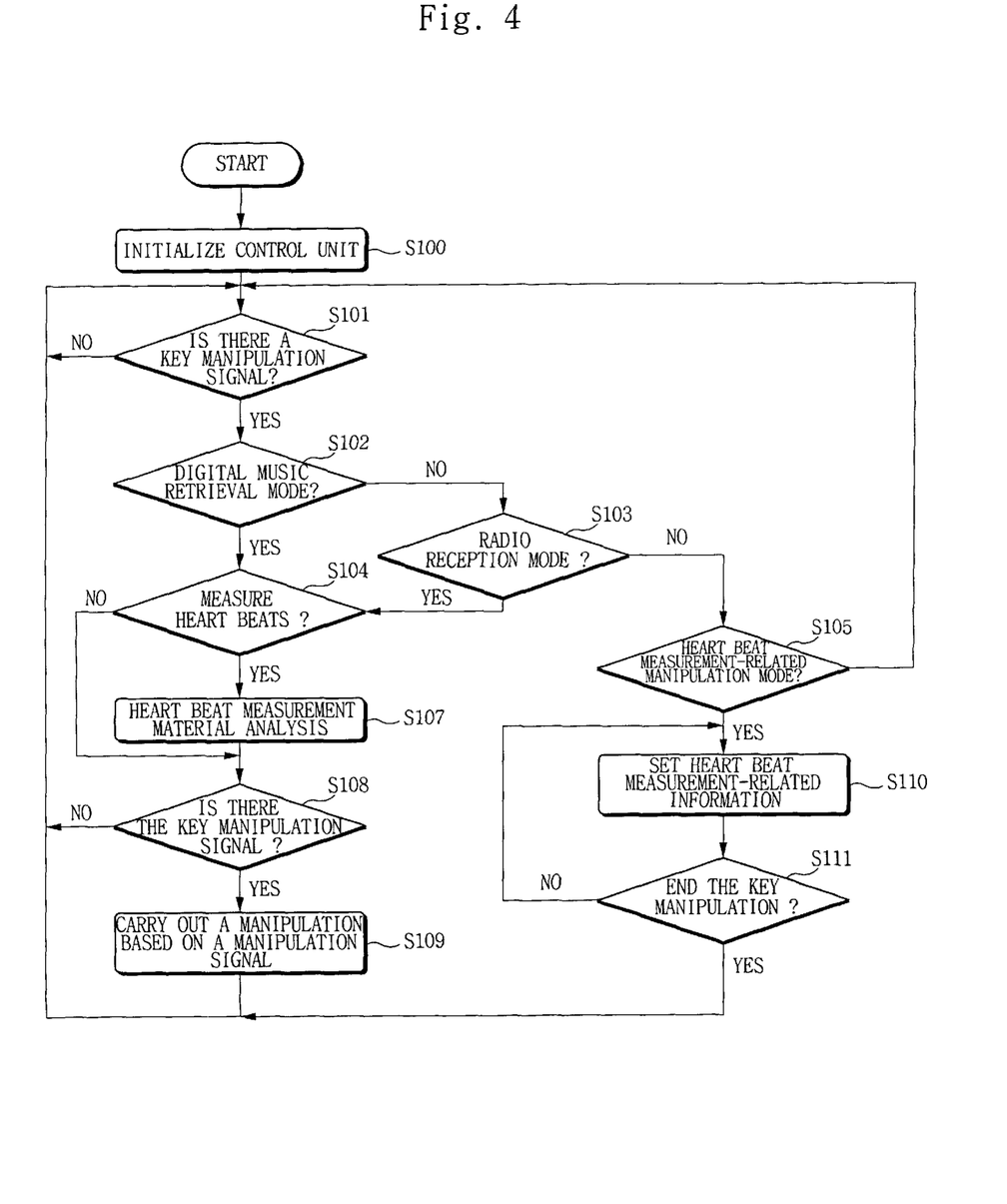
FIG. 4 is a flow chart for showing a process of the heart beat analysis device of FIG. 1.

FIG. 4 is a flow chart for showing a process of the digital music retrieval unit having a heart beat measurement function according to an embodiment of the present invention.

Before carrying out heart beat measurement and music retrieval functions, the control unit 21 initializes the system. Such an initializing process initializes the microcomputer 21b built in the control unit 21 and a register built in the internal of the DSP 21b. Next, the control unit 21 initializes a state register of the radio receiver and an internal state register of the D/A–A/D converter (S100).

Next, the control unit 21 judges if there is a key manipulation signal (S101). Here, the key manipulation signal is to detect if there is a signal based on a key manipulation such as retrieval, stop, volume control, fast forward, rewind, mode setting, hold, and so on, as basic manipulation keys. If there is a key manipulation signal, the control unit 21 carries out a corresponding key function.

In case that the key manipulation signal is a signal for the mode setting, the control unit 21 judges if the mode is a digital music retrieval mode first (S102). The control unit 21 judges if heart beats are measured in case of the digital music retrieve mode as a result of the judgment of the step S102 (S104). If the heart beats are measured as a result of the judgment of the step S104, the control unit 21 carries out a heart beat measurement material analysis subroutine (S107), and judges if a key manipulation signal is inputted after the step S107 (S108), and carries out a corresponding key manipulation signal if there is the key manipulation signal (S109).

Next, if different from the digital music retrieval mode as a result of the step S102, the control unit 21 judges if the key manipulation signal is for a radio reception mode (S103), moves to the step S104 in case of the radio reception mode as a result of the judgment, and carries out the steps after the step S104.

Next, if different from the radio reception mode as a result of judgment of the step S103, the control unit 21 judges if a reference values related to the heart beat measurement are inputted as a heart beat measurement-related manipulation mode (S105), if the reference values related to the heart beat measurement are inputted as a result of judgment, the control unit 21 receives and stores information related to corresponding heart beat measurements. Here, the inputted reference values related to the heart beat measurements are upper and lower limit values measured during physical measurements, whether or not measured data is stored in a memory, information on age, sex, height, and weight of a person to be measured, whether or not messages are outputted in case that physical exercise is not carried out within a set time period, an data output as to a calories consumption during the physical exercise, and so on (S110). The reference values can be automatically set by inputting physical information such as age, sex, height, and weight of a person to be measured in the above.

If the key manipulations in the step S110 are completed, the control unit 21 stores the data values related to the heart beat measurements in the storage unit of the digital music retrieval unit, in order for the person to use an analysis of heart beat changes measured during the physical exercise.

Figure 5:
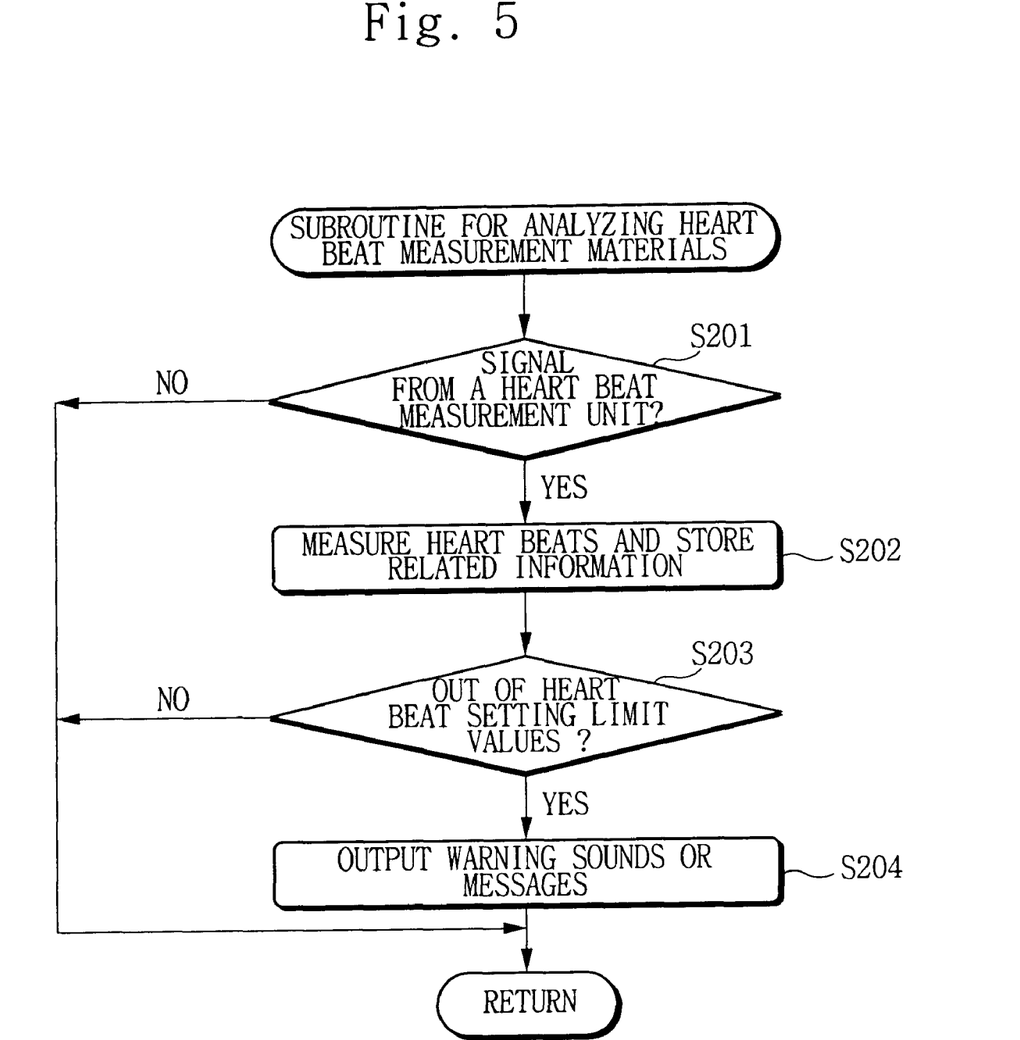
FIG. 5 is a flow chart for showing a heart beat measurement data analysis subroutine of the flow chart of FIG. 4.

FIG. 5 is a flow chart for showing the heart beat measurement material analysis subroutine of FIG. 4.

As shown in FIG. 5, if in the heart beat measurement as a result of judgment in the step S104 of FIG. 4, the control unit 41 judges if the heart beat signal is inputted from a measurement unit (S201). If the heart beat signal is inputted, the control unit 21 stores the inputted heart beat information (S202), compares the inputted heart beat information with the upper and lower limit values of the preset heart beat measurement reference values (S203), and, if out of the range of the values, the control unit outputs warning sounds or messages (S204) and returns to the step S107 for a next process.

Figure 6:
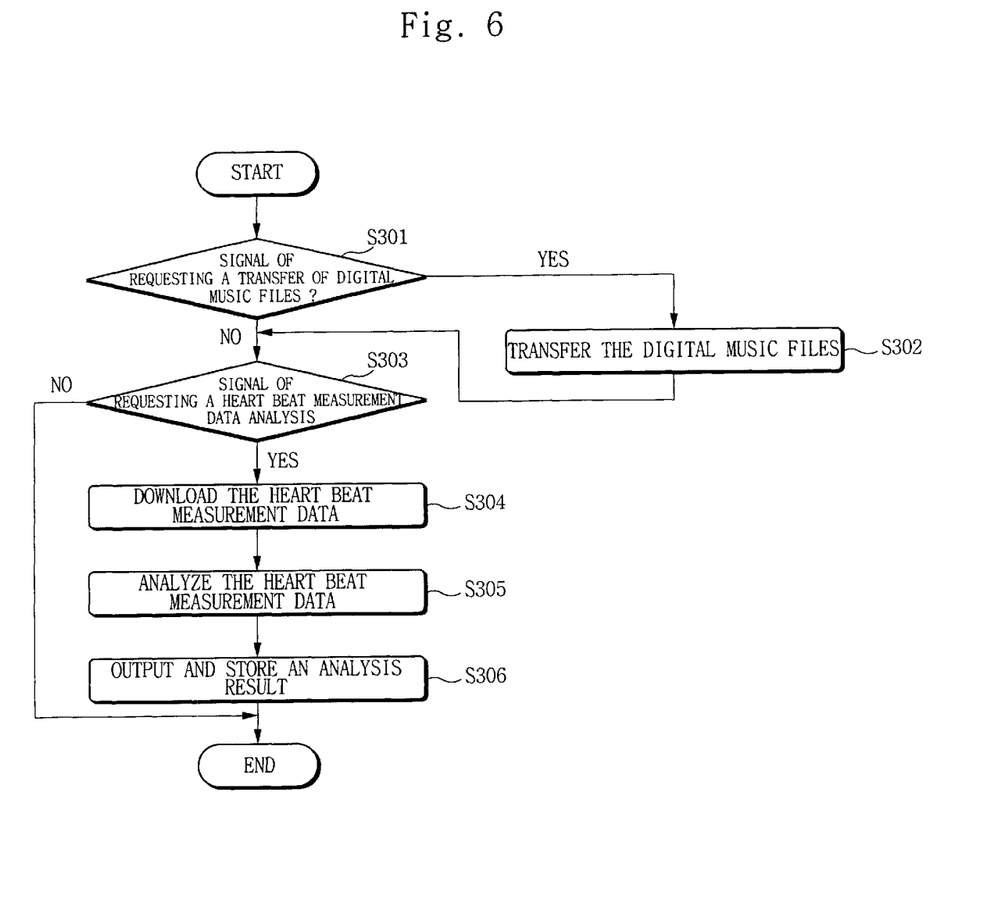
FIG. 6 is a flow chart for showing a process for analyzing heart beat measurement data in a personal computer.

FIG. 6 is a flow chart for showing a process in a personal computer for analyzing user's exercise information stored in the digital music retrieval unit.

As shown in FIG. 6, the control unit 21 judges if a signal for requesting a transfer of a digital music file is inputted from the digital music retrieval unit (S301). If there is no request of the digital music file transfer as a result of the judgment, the control unit 21 performs the step S303, and, if there is the request of the digital music file transfer, the control unit 21 transfers the digital music file to the digital music retrieval unit (S302).

Next, the control unit 21 judges if there is a signal of requesting an heart beat measurement data analysis (S303). The control unit 21 ends its process if there is no signal of requesting the heart beat measurement data analysis as a result of the judgment of the step S303, and downloads the heart beat measurement data from the storage unit of the digital music retrieval unit to the personal computer through the PC connection unit if there is a signal of requesting the heart beat measurement data analysis (S304).

The downloaded heart beat measurement data is stored in the storage unit, and analyzed by a certain program for analyzing the heart beat measurement data (S305). If the analysis is completed, the control unit 21 outputs the analyzed result values through an output unit such as a certain printer, monitor, and so on, stores the result values, and ends its process (S306).

Through the analysis process carried out in the process steps of FIG. 6, changes of the number of heart beats by time (second/minute/hour), changes of the number of heart beats by unit period of time (day/month/year), a suitable exercise amount based on the changes of the number of heart beats, the objective number of heart beats based on age, sex, height, and weight (a suitable exercise amount), a total calories amount consumed in physical exercise, a rate of used body fat to the total calories consumed, and so on, are analyzed for a user (an individual in physical exercise).

The present invention has an effect of preventing a user in physical exercise from becoming easily dull during the exercise, and allows the user to set his suitable exercise amount. Further, the present invention has an effect of preventing the user from excessive exercise by transferring a warning signal to the user in case that the user exceeds the set exercise amount, offering a right exercise amount by analyzing the changes of heart beats based on a user's exercise state as well as measuring an exercise effect, by storing the changes of heart beats of the user in physical exercise and downloading the stored changes of heart beats to a personal computer later.

What is claimed is:
1. A heartbeat analysis method, comprising:
(1) operating, according to a user's selection mode, in any one of
a radio reception mode,
a digital retrieval mode, or
a heartbeat measurement-related information setting mode;
(2) receiving and storing digital music files;
(3 if operating in the heartbeat measurement-related information setting mode, inputting and storing heartbeat reference values;
(4) if operating in the radio reception or digital retrieval mode, using an external unit to measure heartbeat data, including a heartbeat value, of a user during physical exercise;
(5) if operating in the radio reception or digital retrieval mode, determining that the external unit transferred the heartbeat data;
(6) comparing the heartbeat value with the reference values and outputting a signal if the heartbeat value is above an upper limit or below a lower limit of the reference values;
(7) connecting to an external personal computer and transferring the heartbeat data to the personal computer for analysis, where the analysis comprises a determination of
a change degree of the number of heartbeats by time,
a change degree of the number of heartbeats by unit time period,
a suitable exercise amount based on a change in the number of heartbeats,
an exercise effect based on a change in the number of heartbeats,
calories consumed during physical exercise, and
a percentage of body fat decomposition;
(8) outputting and storing the results of the analysis in the personal computer.

2. The heart beat analysis method as claimed in claim 1, wherein inputting the reference values includes the step of inputting at least one of the heart beats during physical exercise, age, sex, height, and weight.

3. The heartbeat analysis method as claimed in claim 1, wherein the external unit comprises a heartbeat measuring means for measuring the heartbeat data of the user in physical exercise, and step 6 comprises
a) using a means having a heartbeat signal processing unit for analyzing measured heartbeat signals from the heartbeat measuring means,
b) comparing the analyzed heartbeat signals with the reference values,
c) outputting warning messages when the user engages in excessive exercise and outputting guidance messages when the user engages in insufficient exercise.

4. The heart beat analysis method as claimed in claim 3, wherein step 2 further comprises using the heart beat signal processing unit for receiving and outputting digital music files when the user selects the digital retrieval mode.

5. The heart beat analysis method as claimed in claim 4, wherein steps 5 and 6 further comprise:
employing a heart beat signal reception unit for receiving heart beat measurement data from the heart beat measuring means;
employing a storage unit for storing the heart beat signal data;
employing an output unit for outputting characters and audio; and
employing a control unit for comparing the heartbeat signals with the reference values if the external unit transferred the heartbeat data, outputting an audio signal or character messages through the output unit if a corresponding result value is less than a lower limit or exceeds an upper limit of the reference values, and outputting an audio signal by digitally processing the digital music files stored in the storage unit if operating in the digital retrieval mode.

6. The heart beat analysis method as claimed in claim 5, wherein using the control unit comprises:
employing a microcomputer for comparing the heart beat measurement data with the reference values and outputting warning and guidance messages; and
employing a digital signal processing unit for retrieving the digital music files stored in the storage unit.

7. The heart beat analysis method as claimed in claim 3, wherein step 1 further comprises providing a radio receiver to the heart beat signal processing unit for receiving and outputting a radio signal when the user selects the radio reception mode.

8. The heart beat analysis method as claimed in claim 7, wherein steps 5 and 6 further comprises:
employing a control unit for comparing the heartbeat signal with the reference values if the external unit transferred the heartbeat data, outputting an audio signal or character messages through the output unit if a corresponding result value is less than a lower limit or above an upper limit of the reference values, and receiving and outputting radio broadcasts if operating in the radio reception mode.

9. The heart beat analysis method as claimed in claim 3, wherein the heart beat measuring means) comprises:
a sensor unit for measuring the heart beats;
a band-pass filter for extracting effective signals for measuring the heart beats from signals detected from the sensor unit;
an amplification unit for amplifying the signals extracted from the band-pass filter; and
a transmission unit for transmitting the amplified signals to an external personal computer.

10. The heart beat analysis method as claimed in claim 3, wherein steps 5 and 6 further comprise:
employing a heart beat signal reception unit for receiving heart beat measurement data from the heartbeat measuring means;
employing a storage unit for storing the heart beat signal data;
employing an output unit for outputting characters and audio; and
employing a control unit for comparing the heartbeat value with the reference values if the external unit transferred the heartbeat data and for outputting an audio signal or character messages through the output unit if a corresponding result value is above the lower limit value or above the upper limit value.

* * * * *